United States Patent [19]

Adams

[11] Patent Number: 4,786,596
[45] Date of Patent: Nov. 22, 1988

[54] METHOD OF PREPARING A TEST STRIP FOR ALCOHOL TESTING

[75] Inventor: Ernest C. Adams, North Webster, Ind.

[73] Assignee: Chem-Elec., Inc., North Webster, Ind.

[21] Appl. No.: 703,335

[22] Filed: Feb. 20, 1985

[51] Int. Cl.[4] .............................................. C12Q 1/28
[52] U.S. Cl. ...................................... 435/28; 435/26; 435/25; 435/192; 435/805; 436/132; 436/169; 436/900; 436/904; 422/56; 422/57
[58] Field of Search ...................... 435/26, 4, 188, 189, 435/190, 192, 28; 472/56, 57; 436/132, 169, 900, 904, 164

[56] References Cited

U.S. PATENT DOCUMENTS 4,110,079  8/1978  Schaeffer et al. ...................... 422/56
4,361,648  11/1982  Shuenn-Tzong ...................... 435/805

FOREIGN PATENT DOCUMENTS 0019937  12/1980  European Pat. Off. .
0117032  8/1984  European Pat. Off. .

OTHER PUBLICATIONS

Singh et al., Anolytica Chimica Acta (1980), vol. 115, pp. 401–405.
Janssen et al., Biochimica et Biophysica Acta (1968), vol. 151, pp. 330–342.

Primary Examiner—Sam Rosen
Attorney, Agent, or Firm—Roger M. Rickert

[57] ABSTRACT

Ethyl alcohol test strip fabricating and use techniques for testing an individual's saliva to determine his sobriety are disclosed. The test strips employ an alcohol oxidase, Peroxidase and an hydrogen donor indicator such as Tetraalkylbenzidine in a carrier matrix supported on the strip with the alcohol oxidase functioning as a catalyst to convert any ethanol present along with ambient oxygen to acetaldehyde and hydrogen peroxide. The peroxidase function as catalyst to induce a color change in the hydrogen donor and convert the hydrogen peroxide to water. The method of fabricating the test strip involves multiple steps of reagent application and hot air drying.

7 Claims, 2 Drawing Sheets

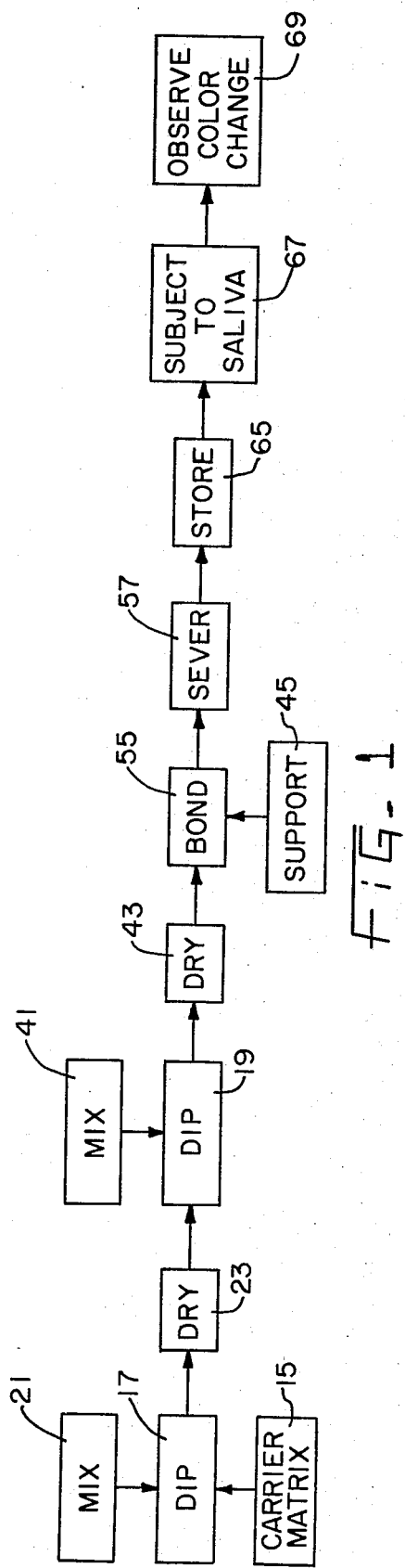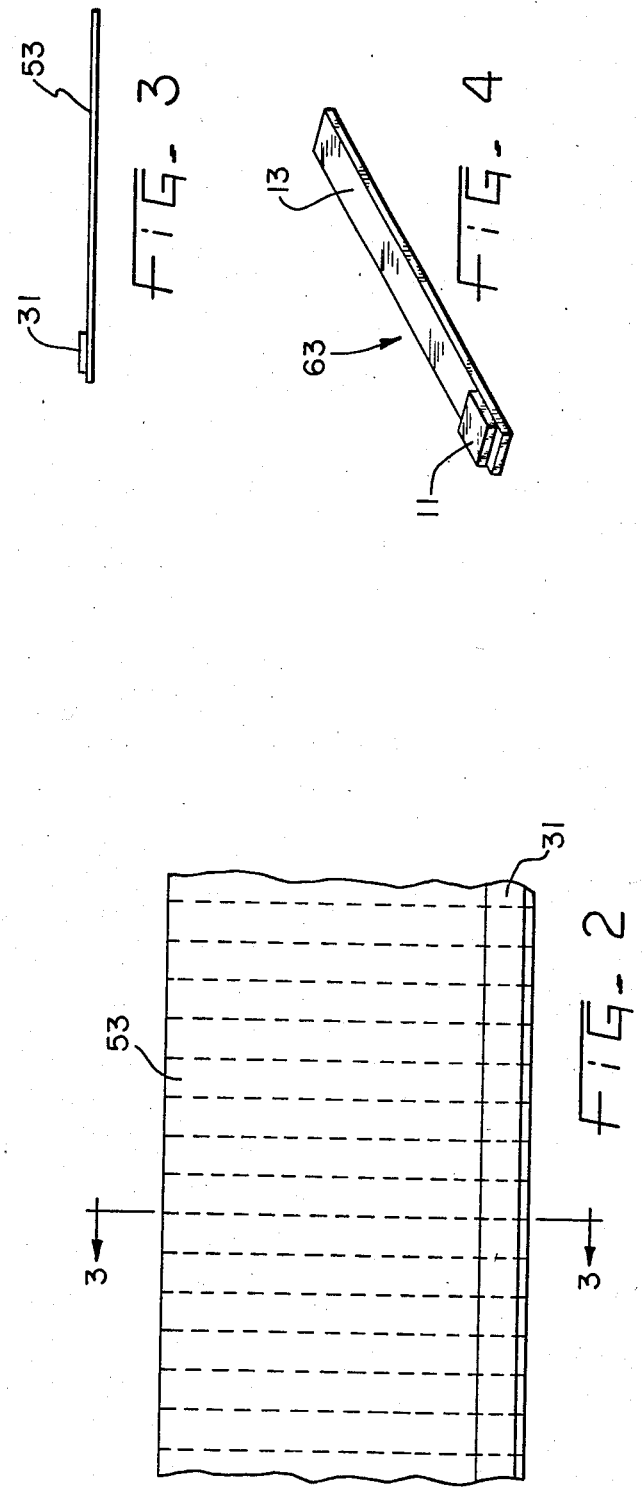

METHOD OF PREPARING A TEST STRIP FOR ALCOHOL TESTING

A BRIEF SUMMARY OF THE INVENTION

The present invention relates generally to the devices and techniques of testing human saliva for traces of foreign substances and in particular for ethanol.

Test strips or sticks which are to be immersed in a sample and include an indicator changing, for example, color in response to the presence of a particular substance being tested for are old and well known including, for example, the familiar litmus and other indicator papers for determining the pH or hydrogen ion concentration of solutions as well as other somewhat more sophisticated test devices for detecting clinically significant substance in biological fluids such as glucose or protein in blood or urine samples.

The desirability of testing individuals to determine the extent to which they are under the influence of alcohol is also very well known. In addition to the familiar drunk driving problem, such tests have significant applicability, for example, in emergency rooms to determine whether an incoming patient is suffering from a serious injury or simply inebriation. Such tests may also be employed by probation officers or other officials and have significant application in industrial settings. Such tests also have wide applicability in agricultural settings such as determining alcohol levels in silage and can even be employed in amateur wine-making.

Numerous schemes for testing an individual to determine the level to which that individual is under the influence of alcohol are also known including the familiar straight line walking, nose touching and balloon inflating techniques which, while being generally qualitative, may be employed by police officers or other officials promptly at any location along with more sophisticated laboratory techniques requiring accurately measured reagents and body fluid samples.

Illustrative of the latter laboratory techniques is U.S. Pat. No. 3,926,736 wherein any of a wide variety of body fluids may be assayed for ethanol content. In this patented scheme ethanol is transformed into acetaldehyde by the action of alcohol dehydrogenase with this reaction, in turn, reducing an NAD indicator to its NADH form with the extent of this reduction being determined by ultraviolet colorimetry providing the ultimate indication of alcohol content in the body fluid tested. The techniques of this patent require the reagents to be freeze dried in a fine powder form preferably in two different portions with premeasured quantities of each dissolved in water at the time the assay is to be carried out. Such an arrangement, while well suited to laboratory conditions, is ill-suited to, for example, on-site testing of automobile drivers by police officers to determine the level of recent alcohol ingestion on the part of the driver.

Alcohol dehydrogenase as employed in the above-mentioned patent scheme is an enzyme also found in the human liver where it functions to catalyze the same reaction employed in the patented arrangement. This enzyme is also employed in substantially the same way in the scheme disclosed in U.S. Pat. No. 3,493,467. This patented arrangement, like the first, is rather complex and limited to a laboratory environment.

As contrasted with the above two patented schemes, test strips or sticks are not strictly laboratory procedures but are adaptable to use in the home and by comparatively unskilled users. Urine sugar level test strips, for example, are commercially available for home use.

A rather complete discussion of test strips as to both their chemistry and techniques of manufacture and use may be found in commonly owned U.S. Pat. Nos. 4,361,648 and 4,362,697 with both patented arrangements suggesting among others the use of 3,3',5,5'-tetramethylbenzidine. These commonly owned patented schemes are concerned with testing a wide variety of body fluids for cholesterol, glucose and dextrose and include the suggestion of peroxidase and peroxidase-like substances as catalysts in promoting the color change reaction on the indicator. While test strips per se are suitable for use outside the laboratory, many of the techniques disclosed in these commonly known patents are solely laboratory techniques.

Among the several objects of the present invention may be noted the provision of a simplistic ethyl alcohol level testing scheme; the provision of a composition of matter which may be economically produced and conveniently stored for subsequent use as an alcohol level testing material; the provision of a test strip manufacturing process and subsequent process of using that test strip to determine the level to which an individual is under the influence of alcohol; and overall improvements and simplifications in the techniques for testing a person to determine insobriety. These as well as other objects and advantageous features of the present invention will be in part apparent and in part pointed out hereinafter.

In general, alcohol testing, according to the present inventive techniques, includes the preliminary steps of impregnating a carrier matrix with an enzyme which catalyzes a reaction converting ethyl alcohol to an oxidizing agent along with an indicator which changes color when oxidized. The carrier matrix is then stored in a substantially dry condition until needed for testing. Testing is accomplished by subjecting the carrier matrix to saliva from the individual and observing the color variation induced by the presence of ethyl alcohol within the saliva.

Also, in general, and in one form of the invention, a person's sobriety is determined by subjecting a chemically impregnated carrier to the person's saliva and observing any color change of that carrier induced by the presence of ethanol within the saliva. The carrier may, for example, be impregnated with a mixture including an enzyme for catalyzing a reaction which converts the ethanol as present in the saliva and ambient oxygen to acetaldehyde and hydrogen peroxide and an indicator such as tetraalkylbenzidine and a peroxidatively active substance such as peroxidase for catalyzing a color changing reaction between the hydrogen peroxide and indicator. Preferably, the step of subjecting the carrier to the person's saliva is performed orally directly on the person being tested.

Further, in general and in one form of the invention, a composition of matter suitable for testing human saliva to determine the ethyl alcohol content thereof includes an alcohol oxidase, peroxidase and a hydrogen donor which changes color when oxidized. The composition of matter may further include materials having thickening, stabilizing and buffering properties.

BRIEF DESCRIPTION OF THE DRAWING

FIG. 1 is a functional block diagram illustrating the overall testing method of the present invention from initial mixing of the components and fabrication of the test strips through to completion of the test on an individual;

FIG. 2 is a plan view of partially completed test strips in accordance with the present invention;

FIG. 3 is a view in cross-section along lines 3—3 of FIG. 2;

FIG. 4 is a perspective view of a completed test strip;

Corresponding reference characters indicate corresponding parts throughout the several views of the drawing.

Figure 5:
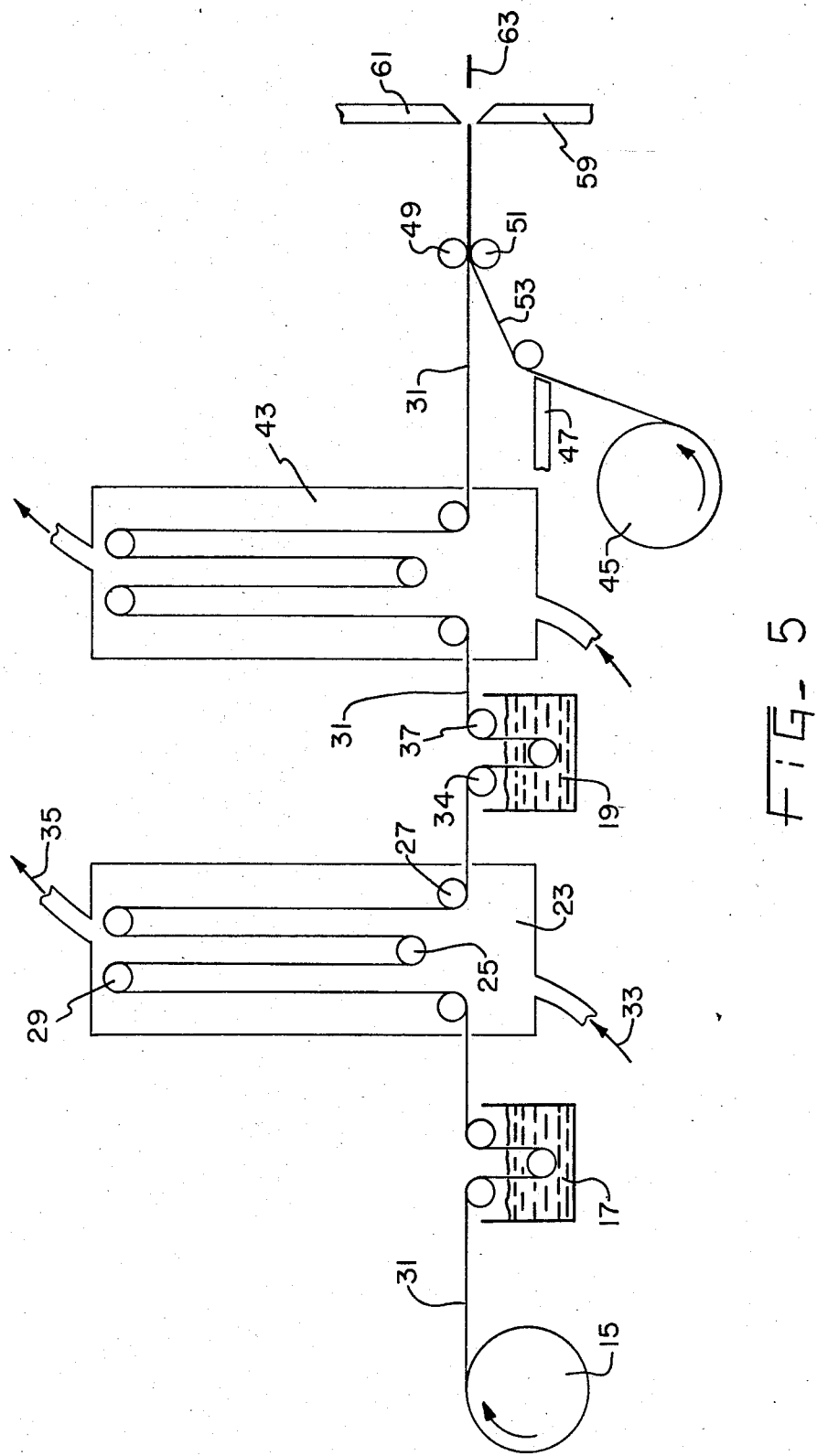
FIG. 5 is a simplified elevation view of apparatus for performing the preliminary manufacturing steps in the process of FIG. 1.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

FIG. 4 illustrates the product which is the object of the manufacturing portion of the present inventive method. This product has a carrier matrix 11 impregnated with a composition of matter to perform the desired testing function with that carrier matrix being bonded to a support strip 13 such as polyester or other paper or plastic material which is inert as far as any reactions are concerned and functions simply as a means for manipulating the carrier matrix 11. Strip 13 may, for example, be on the order of two inches in length and one eighth to one quarter inch in width and of any convenient thickness such as 5 to 10 thousandths of an inch with this thickness being somewhat exaggerated in FIG. 3. The carrier matrix 11 may be any of a wide variety of materials as, for example, suggested in the aforementioned U.S. Pat. No. 4,362,697 patent. Simple chemical filter paper has been successfully used and will be referred to for the purpose of this description.

A roll source of filter paper is illustrated at 15 in FIGS. 1 and 5. A two stage dipping process at 17 and 19 in FIGS. 1 and 5 will be described; however, as will be apparent from some of the subsequent examples, the impregnating of the carrier matrix 11 may, in some cases, be accomplished by a single dipping step. The preparatory or preliminary steps involved in fabricating the test strip of FIG. 4 may now be followed while referring to FIGS. 1 and 5.

The roll source of the carrier matrix 15 is a strip of conventional filter paper on the order of one-quarter to one-half inch in width, however, wider strips to be subsequently severed could be employed. This strip of filter paper is passed through a bath or dip 17 to impregnate the filter paper with certain of the components of the present inventive composition of matter which components were premixed as indicated at 21. Subsequent to the dipping 17, the filter paper strip is dried at 23 by a stream of hot air. For example, the strip 31 may pass over a series of driven and idler rollers such as 25, 27 and 29 so as to execute a lengthy circuitous path through a comparatively tall oven through which hot air is passed as indicated by the arrows 33 and 35. Thereafter, strip 31 passes around further rollers 37 and 34 through a second dip process 19 to absorb the additional composition of matter components which were premixed as at 41. The strip of filter paper 31 is then subjected to a second similar air drying operation 43 at which time the strip now carries in dry state all of the components of the composition of matter. The ovens could extend horizontally rather than vertically, if desired.

A roll of support material 45, such as polyester or other inert plastic, is fed past a wick 47 which applies a thin strip of adhesive material thereto and then this support material 53 and impregnated filter paper strip 31 are pressed together as between pinch rollers 49 and 51 to bond strip 31 to the support strip 53. Subseqeunt to this passage through the pinch rollers 49 and 51, the composite strip appears as in FIG. 2 as a result of the bonding operation 55. Subsequently, the strip of FIG. 2 is subjected to a severing operation 57 as by knives 59 and 61 which repeatedly sever individual test strips along the vertical dotted lines of FIG. 2 to provide thereafter for accumulation and storage of individual test strips 63. These individual strips may be stored in a dry condition as at 65 for packaging individually or in groups for subsequent use as desired.

Strip use may be by directly subjecting the strip orally to the saliva of a person being tested or otherwise subjecting the strip to an individual's saliva as indicated at 67 and thereafter observing and color change which may occur as indicated at 69. Preferably, the strip 63 is supplied with a color chart so that the color change in the carrier matrix portion 11 of the strip 63 may be compared with that chart for the particular composition of matter employed to provide a fairly accurate indication of the alcohol concentration within the saliva of the individual tested. For example, the particular composition of matter referred to in Example 1, subsequently, a green to blue coloration occurs with an intensity proportional to the alcohol concentration.

EXAMPLES

The following examples illustrate suitable components which may be mixed in the mixing steps 21 and 41 or in some cases in a single mixing step and is shown merely by way of example, and not to be construed as limiting the scope of the invention. Each of these examples refers to alcohol oxidase, an enzyme material more completely described in U.S. Pat. No. 4,430,427 and the references cited therein. The examples also refer to peroxidase with this and suitable other peroxidatively active substances being described in greater detail, for example, in the aforementioned U.S. Pat. No. 4,361,648.

Example 1

| | |
|---|---|
| Algin | 10 mg. |
| Alcohol Oxidase | 100 units |
| Peroxidase | 500 Units |
| Gelatin | 20 mg. |
| Tris-Malonate Buffer (pH 7.2 1 M) | 1 ml. |
| Water | 1 ml. |

The strip of filter paper is dipped (17 in FIG. 1) into the above mixture and dried as at 23 with the composition of the second dip 19 as follows:

| | |
|---|---|
| 3,3,5,5 Tetramethylbenzidine | 31 mg. |

| -continued | |
|---|---|
| xylene | 2 ml |

The mixing step 41 of FIG. 1 for this second dip 19 is as follows:

40 mg. Tetramethylbenzidine dihydrochloride is dissolved in 2 ml. water. The solution is decolored with 0.01 ml. cystine hydrochloride 10 mg/ml. Two ml. xylene is added and then the hydrochloride is neutralized by the addition of sodium hydroxide. The tetramethylbenzidine is extracted into the xylene by repeated inversions. The xylene layer is separated and dried with calcium chloride. The xylene solution of tetramethylbenzidine is used to impregnate the already once dipped strips described above. The strips are dried with a stream of hot air. The resulting strips are mounted on a plastic sheet with suitable adhesive and cut into sticks. The sticks give a green to blue color with alcohol, the intensity proportional to alcohol concentration.

Example 2

Same as Example 1 except that the tetramethylbenzidine in the second dip is reduced to 10 mg. This gives a stick that, with the higher levels of alcohol, has a brown or black color that is distinctively different from the blue of the lower levels.

Examples 1 and 2 are currently recognized as being noncarcinogenic and are, therefore, presently preferred embodiments of present invention.

Example 3

| | |
|---|---|
| Algin | 10 mg. |
| Alcohol oxidase | 100 Units |
| Peroxidase | 500 Units |
| Gelatin | 20 mg. |
| 3-Methyl-2-Benzothiazolinone Hydrazone Hydrochloride | 3.8 mg. |
| Dimethylaminobenzoic Acid | 1.2 mg. |
| Tris-Malonate buffer (pH 7.2, 1 M) | 1 ml. |
| Water | 1 ml |

Strips of filter paper are dipped into the mixture and dried in a stream of hot air. The strips are mounted on plastic with adhesive and cut into sticks.

Example 4

Same as Example 1, except the tetramethylbenzidine is replaced by o-tolidine.

Example 5

Same as Example 1, except that the tetramethylbenzidine is replaced by an equal mixture of o-tolidine and dianisidine.

Example 6

Same as Example 1, except that the buffer is a phosphate.

Example 7

| | |
|---|---|
| Algin | 10 mg. |
| Alcohol oxidase | 100 Units |
| Peroxidase | 500 Units |
| Gelatin | 20 mg. |
| 2,2'-azinodi-(3-Ethyl-benzthiazoline Sulfonic Acid) Diamonium salt | 40 mg. |
| Tris-Malonate buffer (pH 7.2, 1 M) | 1 ml. |
| Water | 1 ml. |

Strips of filter paper are dipped in the mixture and dried in a stream of hot air. The strips are mounted on plastic with adhesive and cut into sticks. The example provides a hydrogen donor 2,2'-Azinodi-(3-Ethylbenzthiazoline Sulfonic Acid) commonly known as ABTS.

Example 8

| | |
|---|---|
| Algin | 10 mg. |
| Alcohol Oxidase | 100 units |
| Peroxidase | 500 units |
| Gelatin | 20 mg. |
| 4-Aminophenazone | 8 mg |
| 3,4-Dichlorophenol | 40 mg. |
| Tris-Malonate buffer (pH 7.2, 1 M) | 1 ml. |
| Water | 1 ml. |

The pH values can vary over a range of 5 to 8 in each of the foreging examples. While Algin and Gelatin are disclosed as thickeners and stabilizers, other materials may be employed. Further variations such as wetting agents, for example, Triton X-100, Brij-35, and Tween 80 may be employed to improve the homogeneity and to increase penetration of the composition of matter into the carrier matrix. Mixture of the inventive composition of matter may be with a soluble plastic such as cellulose acetate, cellulose nitrate, acrylamide or similar materials stripped on a backing material and the solvent allowed to evaporate.

From the foregoing it is now apparent that a novel test strip fabrication and use technique as well as a unique composition of matter suitable for use in such techniques have been disclosed meeting the objects and advantageous features set out hereinbefore as well as others and that modifications as to the precise configurations, shapes, components and details may be made by those having ordinary skill in the art without departing from the spirit of the invention or the scope thereof as set out by the claims which follow.

What is claimed is:

1. A method of making a test strip for use in determining the level to which an individual is under the influence of alcohol by subjecting the strip to saliva from the individual and then observing a change in the coloration of the strip the intensity of which is proportional to the alcohol concentration in the saliva, the method comprising the steps of:

impregnating a carrier matrix with an alcohol oxidase enzyme which catalyzes a reaction converting ethanol to an oxidizing agent, and a hydrogen donor indicator which changes color when oxidized; by first immersing the carrier matrix in a solution consisting of alcohol oxidase, a peroxidatively active substance and a buffer; hot air drying the carrier matrix after immersion; immersing the previously hot air dried carrier matrix in a solution consisting of a hydrogen donor and a solvent therefor; and again hot air drying the carrier matrix; and storing the impregnated matrix in a substantially dry condition until the time of testing.

2. The method of claim 1 wherein the step of immersing the previously hot air dried carrier matrix comprises immersion in a xylene solution containing tetramethylbenzidine.

3. The method of claim 1 wherein the hydrogen donor is 2,2'-azinodi-(3-ethylbenzthiazoline sulfonic acid).

4. The method of claim 1 wherein the hydrogen donor is a mixture of 3-methyl-2-benzothiazolinone hydrazone and 3-dimethylaminobenzoic acid.

5. The method of claim 1 wherein the hydrogen donor is a mixture of 3,4-dichlorophenol and 4-aminophenazone.

6. The method of claim 1 wherein the hydrogen donor is o-tolidine.

7. The method of claim 1 wherein the hydrogen donor is a mixture of o-tolidine and dianisidine.

* * * * *